United States Patent
Stewart et al.

(10) Patent No.: US 12,408,883 B2
(45) Date of Patent: Sep. 9, 2025

(54) X-RAY IMAGING SYSTEM FOR PIPE WELD

(71) Applicant: QUANTIVE GROUP LLC, Tulsa, OK (US)

(72) Inventors: Alex Stewart, San Francisco, CA (US); Moses Wekwete, Spring, TX (US)

(73) Assignee: QUANTIVE GROUP LLC, Tulsa, OK (US)

(*) Notice: Subject to any disclaimer, the term of this patent is extended or adjusted under 35 U.S.C. 154(b) by 179 days.

(21) Appl. No.: 18/040,755

(22) PCT Filed: Aug. 5, 2021

(86) PCT No.: PCT/EP2021/071869
§ 371 (c)(1),
(2) Date: Feb. 6, 2023

(87) PCT Pub. No.: WO2022/029227
PCT Pub. Date: Feb. 10, 2022

(65) Prior Publication Data
US 2023/0277150 A1    Sep. 7, 2023

Related U.S. Application Data

(60) Provisional application No. 63/062,018, filed on Aug. 6, 2020.

(51) Int. Cl.
*A61B 6/00* (2024.01)
*A61B 6/02* (2006.01)
*A61B 6/42* (2024.01)

(52) U.S. Cl.
CPC .............. *A61B 6/482* (2013.01); *A61B 6/025* (2013.01); *A61B 6/4241* (2013.01)

(58) Field of Classification Search
CPC ....... A61B 6/482; A61B 6/025; A61B 6/4241; G01N 2223/3303; G01N 2223/413; G01N 2223/628; G01N 2223/629; G01N 23/04
See application file for complete search history.

(56) References Cited

U.S. PATENT DOCUMENTS 2,475,596 A * 7/1949 Dawson ................. G01N 23/04
219/92

FOREIGN PATENT DOCUMENTS

| WO | 2010/033265 | 3/2010 |
| WO | 2020/073132 | 4/2020 |

OTHER PUBLICATIONS

International Search Report and Written Opinion issued in corresponding International Patent Application No. PCT/EP2021/071869, dated Jan. 5, 2022.

* cited by examiner

*Primary Examiner* — Kiho Kim
(74) *Attorney, Agent, or Firm* — Pillsbury Winthrop Shaw Pittman LLP

(57) ABSTRACT

An x-ray imaging system comprises an x-ray emitter for emitting a beam of x-ray photons in a projection pattern, a first photon detector, a second photon detector, and an orbital travel assembly. The first photon detector and second photon detector are configured for sensing a first detection pattern of photons and a second detection pattern of photons, respectively, emitted from the x-ray emitter and passing through a portion of the weld. The orbital travel assembly is configured for supporting the x-ray emitter and the first and second photon detectors The second photon detector is positioned behind the first photon detector in a direction of travel along an orbital weld path, such that the second photon detector is configured to sense the second detection pattern after the first photon sensor detects the first detection pattern, in use.

12 Claims, 7 Drawing Sheets

X-RAY IMAGING SYSTEM FOR PIPE WELD

CROSS REFERENCE TO RELATED APPLICATIONS

This patent application is the U.S. National Phase of International Patent Application No. PCT/EP2021/071869, filed Aug. 5, 2021, which claims priority to U.S. Provisional Patent Application No. 63/062,018, filed on Aug. 6, 2020. The subject matter of each is incorporated herein by reference in its entirety.

BACKGROUND OF THE INVENTION

The present invention relates to an apparatus for and method of generating an x-ray image of a pipe weld for detecting a defect in the pipe weld. Pipelines can be made up of many thousands of pipe segments welded together end to end. With hazardous and/or toxic material to be transported through the pipeline, the quality and integrity of the welds is important. Therefore, after a weld is built, an operator may perform non-destructive testing on the welds to generate an internal structural x-ray image from which a weld defects might be detected. One such defect detection method includes taking an x-ray of the weld and having an operator review/inspect the x-ray visually to see if any anomalies appear on the image. One apparatus presently used to generate x-ray weld images includes an x-ray emitter which emits a beam of x-ray photons though a portion of the weld. Not all of the photons emitted from the source pass through the weld, but the portions of the beams that do pass through the weld, pass through the weld in a pattern related to the structural integrity of the weld. On an opposite side of the weld from the emitter is a detector having a generally planar sensor (e.g., light or photo sensor) which detects the pattern of photons that passed through the weld. The sensor collects data that represents the photon pattern. The data of the photon pattern can then be processed to generate an image of the weld to be assessed by an inspector. The inspector may identify possible defects on the image (e.g., related to observed areas of contrast). One arrangement of equipment presently used in the industry is shown in FIG. 1. FIG. 1 shows an inspection system 100 mounted to a pipe/pipeline 120. Inspection system 100 includes x-ray transmitter/emitter 140 and an x-ray detector or receiver 160. X-ray transmitter 140 and x-ray receiver 160 are rollably connected to a track 170 that is mounted to and round the outer wall of pipeline 120. Specifically, transmitter 140 and receiver 160 are mounted to track 170 and are positioned at and remain at polar opposite sides of pipeline 120. Both transmitter 140 and receiver 160 may be self-propelled (e.g., by electric stepper motors) and inspection system 100 may include a computer controller to control transmitter 140 and receiver 160 in conjunction. Specifically, the controller may move transmitter 140 and receiver 160 in a same orbital direction D in order to maintain their relative polar opposite relationship. Therefore, when assembled and when transmitter 140 emits an x-ray beam toward receiver 160, the beam passes through both a portion of the pipe wall nearest transmitter 140 and a portion of the pipe wall nearest receiver 160. However, the photon pattern detected by receiver 160 is related to the portion of the pipe weld nearest receiver 160.

In such an x-ray equipment arrangement only a limited number of photons pass through the weld portion to be detected. The amount of photons that pass through the weld directly affects the potential quality of the weld image to be produced for inspection. The more photons pass through the weld, the higher the contrast and general quality of the final weld image. It would be beneficial if a additional photon pattern data generation capacity could be included on a structure similar to the existing (above described) conventional inspection systems 100. It would also be beneficial if the additional data generated could be processed and combined with the existing photon pattern data to generate a single image of better quality and contrast than could be generated from the original data. Furthermore, it would be beneficial if the data from both photon patterns could be detected, recorded and stored in the time it took for a single revolution of the transmitter 140 and receiver 160 around track 170.

SUMMARY OF THE INVENTION

A first aspect of the present invention provides an x-ray imaging system for generating images of a pipe weld from which weld quality defects may be detected, according to Claim 1 of the appended claims.

A second aspect of the invention provides a method of generating an x-ray image of a pipe weld for detecting a defect in the weld by inspection of the x-ray image, according to Claim 8.

A third aspect of the invention provides an x-ray imaging system for generating images of a pipe weld from which weld quality defects may be detected, according to Claim 11.

Preferred, and other optional, features of the invention are defined and described in the dependent claims.

It is to be understood that any feature, including any preferred or other optional feature, of any aspect of the invention, may be a feature, including a preferred or other optional feature, of any other aspect of the invention.

According to an aspect of the invention, an x-ray system is provided for generating images of a pipe weld from which weld quality defects may be detected, the system includes an x-ray emitter, a first photon detector, a second photon detector, and an orbital travel assembly. The x-ray emitter is for emitting a beam of x-ray photons in a projection pattern. The first photon detector is for sensing a first detection pattern of photons emitted from the x-ray emitter and that pass through a portion the weld. The second photon detector senses a second detection pattern of photons emitted from the x-ray emitter and that passing through the same portion of the weld. The orbital travel assembly rollably and orbitally supports the x-ray emitter and the first and second photon detectors as they travel along an orbital weld path of the weld. The second photon detector may be positioned downstream of the first photon detector along the orbital weld path; and the second photon detector may sense the second detection pattern after the first photon sensor detects the first detection pattern.

Another aspect of the invention provides an x-ray imaging system for generating images of a weld from which weld quality defects may be detected, the system comprising: an x-ray emitter for emitting a beam of x-ray photons in a projection pattern; a first photon detector for sensing a first detection pattern of photons emitted from the x-ray emitter and passing through a portion the weld; a second photon detector for sensing a second detection pattern of photons emitted from the x-ray emitter and passing through the portion of the weld; an orbital travel assembly for supporting the x-ray emitter and the first and second photon detectors as they travel along an orbital weld path of the weld; wherein the second photon detector is positioned downstream of the first photon detector along the orbital weld path; and wherein the second photon detector senses the second detection pattern after the first photon sensor detects the first detection pattern.

Another aspect of the invention provides a sensing module for use in the x-ray imaging system of the invention, the sensing module including: a module housing; the module housing containing a first electronic sensing module; the first electric sensing module electrically connected to the first sensing module; the first sensing module including an upwardly directed photon receiving face for sensing the first detection pattern.

The module housing preferably further contains a second electronic sensing module; the second electronic sensing module electrically connected to the second sensing module; the second sensing module including an upwardly directed photon receiving face for sensing the second detected pattern.

The first electronic sensing module preferably is positioned relative to the second electronic sensing module in order to detect a mirror image of the second detection pattern.

A memory device preferably receives and records data representing the first detection pattern and data representing the second detection pattern.

The data representing the first detection pattern preferably is projected onto a visual display and the date representing the second detection pattern is simultaneously also projected onto the visual display to superimpose the first and second detection patterns.

The position of the first detection pattern preferably is adjusted with respect to the position of the second detection pattern in order to match the images and correct for the offset caused by the second detection pattern being generated after the first detection pattern.

Another aspect of the invention provides a method of generating an x-ray image of a weld for detecting a defect in the weld by inspection of the x-ray image including the steps of: providing an x-ray photon emitter; providing a first photon detector for sensing a first detection pattern of photons projected from the x-ray photon emitter; providing a second photon detector for sensing a second detection pattern of photons projected from the x-ray photon emitter; projecting photons from the x-ray photon emitter through a portion of a weld and onto the first photon detector to sense the first detector pattern and generate data representing the first detector pattern; after detecting the first detector pattern, projecting photons from the x-ray photon emitter through the portion of the weld and onto the second photon detector to sense the second detector pattern and generate data representing the second detector pattern; superimposing the first detector pattern onto the second detector pattern and adjusting the two patterns for offset so that the first detector pattern is synced with the second detector pattern.

The step of superimposing the first detector pattern onto the second detector pattern and adjusting the two patterns for offset so that the first detector pattern is synced with the second detector pattern, preferably is the step of superimposing the first detector pattern onto the second detector pattern by adjusting the offset position of the two patterns in a direction of travel so that the first detector pattern is synced in the direction of travel with the second detector pattern.

The step of superimposing the first detector pattern onto the second detector pattern and adjusting the two patterns for offset so that the first detector pattern is synced with the second detector pattern, preferably is the step of superimposing the first detector pattern onto the second detector pattern by adjusting the offset position of the two patterns in a transverse direction which is transverse to a direction of travel so that the first detector pattern is synced in the transverse direction with the second detector pattern.

Another aspect of the invention provides an x-ray imaging system for generating images of a weld from which weld quality defects may be detected, the system comprising: an x-ray emitter for emitting a beam of x-ray photons in a projection pattern; a photon detector for sensing a first detection pattern of photons emitted from the x-ray emitter and passing through a portion the weld; an orbital travel assembly for supporting the x-ray emitter and the photon detector as they travel along an orbital weld path of the weld; an image processing computer; wherein the photon detector senses a first detector pattern of photons passing through the portion of the weld and the image processing computer stores data associated with the first detection pattern; and wherein the image processing computer uses the first detection pattern and the geometry of the relative positions of the portion of the weld and the photon detector to generate a second detection pattern; and wherein the second detection pattern is associated with a location of the portion of the weld in the direction of thickness of the pipe that is a distance from the outer surface of the pipe.

The image processing computer preferably also uses the position of the x-ray emitter relative to the portion of the weld and/or relative to the photon detector to generate the second detector pattern.

The image processing computer preferably uses the first detector pattern and the geometry of the relative positions of the portion of the weld and the photon detector to generate a plurality of second detector patterns, each of the second detector patterns associated with a location of the portion of the weld in the direction of thickness of the pipe;

The image processing computer preferably processes data from the first detector pattern and/or the plurality of detector patterns to determine the location of one or more defects or anomalies.

Advantageously, one or more defects is identified and the image processing computer determines in which of the plurality of detector patterns the defect is best focused.

Preferably, an image of the portion of the weld is displayed and the location of the defect in the direction of thickness is identified.

DETAILED DESCRIPTION OF THE PREFERRED EMBODIMENTS

Figure 1:
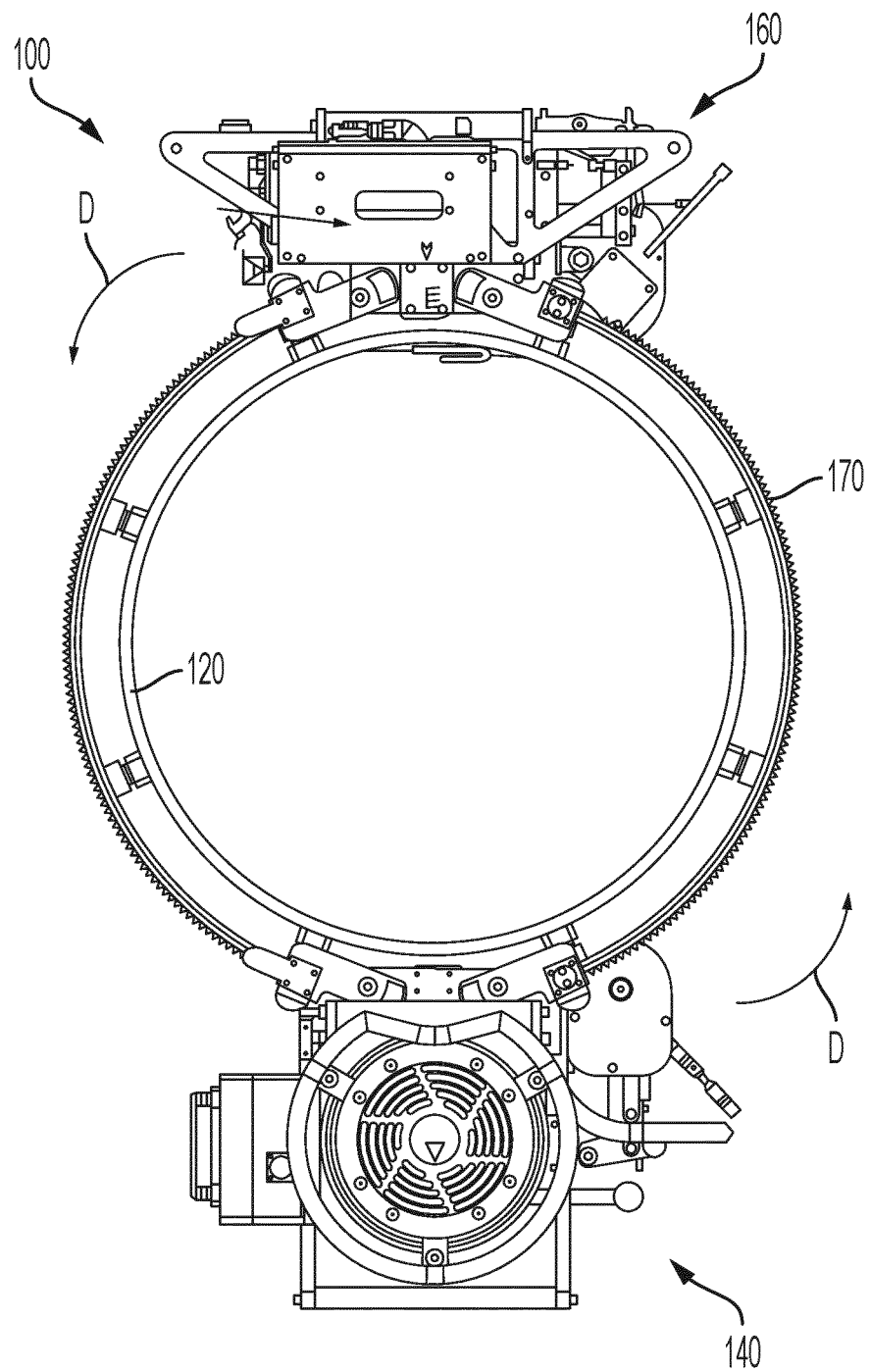
FIG. 1 shows a prior art inspection system looking down a longitudinal central axis of the pipe.
Figure 2:
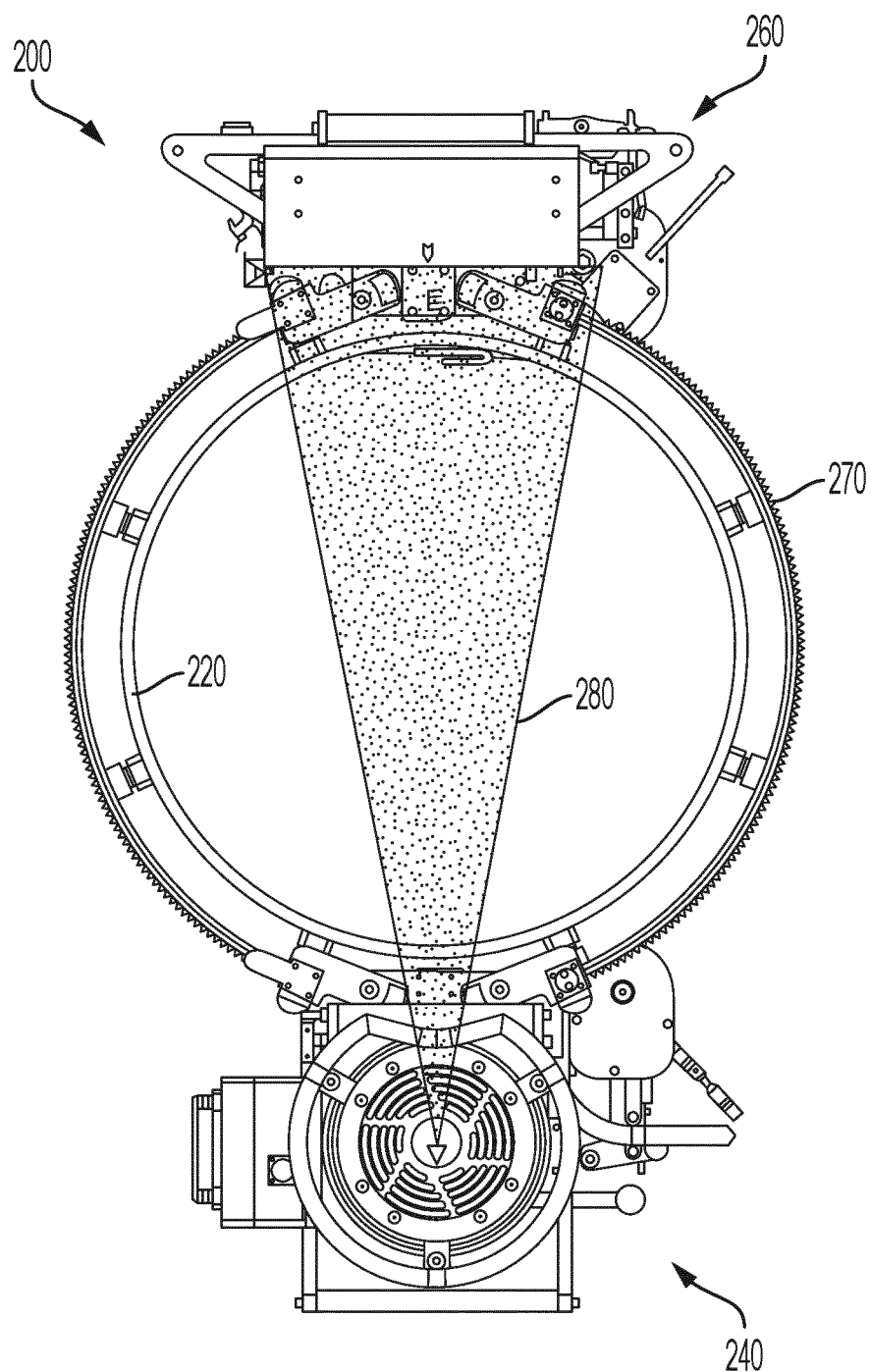
FIG. 2 show an inspection system of the present invention looking down a longitudinal axis of the pipe and showing an x-ray beam.

The present invention inspection system 200 is shown in FIG. 2. FIG. 2 shows an inspection system 200 mounted to a pipe/pipeline 220. Inspection system 200 includes x-ray transmitter/emitter 240 and an x-ray detector or receiver 260. X-ray transmitter 240 and x-ray receiver 260 are rollably connected to a track 270 that is mounted to and round the outer wall of pipeline 220. Specifically, transmitter 240 and receiver 260 are mounted to track 270 and are positioned at and stay at polar opposite sides of pipeline 220. Both transmitter 240 and receiver 260 may be self-propelled and controlled in conjunction by a controller in order to move them in a same orbital direction D in order to maintain their relative polar opposite relationship. Therefore, when assembled and when transmitter 240 emits an x-ray beam 280 toward receiver 260, beam 280 passes through both a portion of the pipe wall nearest transmitter 240 and a portion of the pipe wall nearest receiver 260. In any case, the photon pattern detected by receiver 260 is related to the portion of the pipe weld nearest to receiver 260 (i.e., farthest from transmitter 240).

While the inspection system 200 may be in the form of the above-described Double Wall Single Image (DWSI) configuration (i.e., emissions pass from outside the pipe through two walls to a sensor on the outside of the pipe). Concepts contemplated by this disclosure may also include a Single Wall Single Image configuration (i.e., X-ray source is inside the pipe and emissions pass through the pipe).

Figure 3:
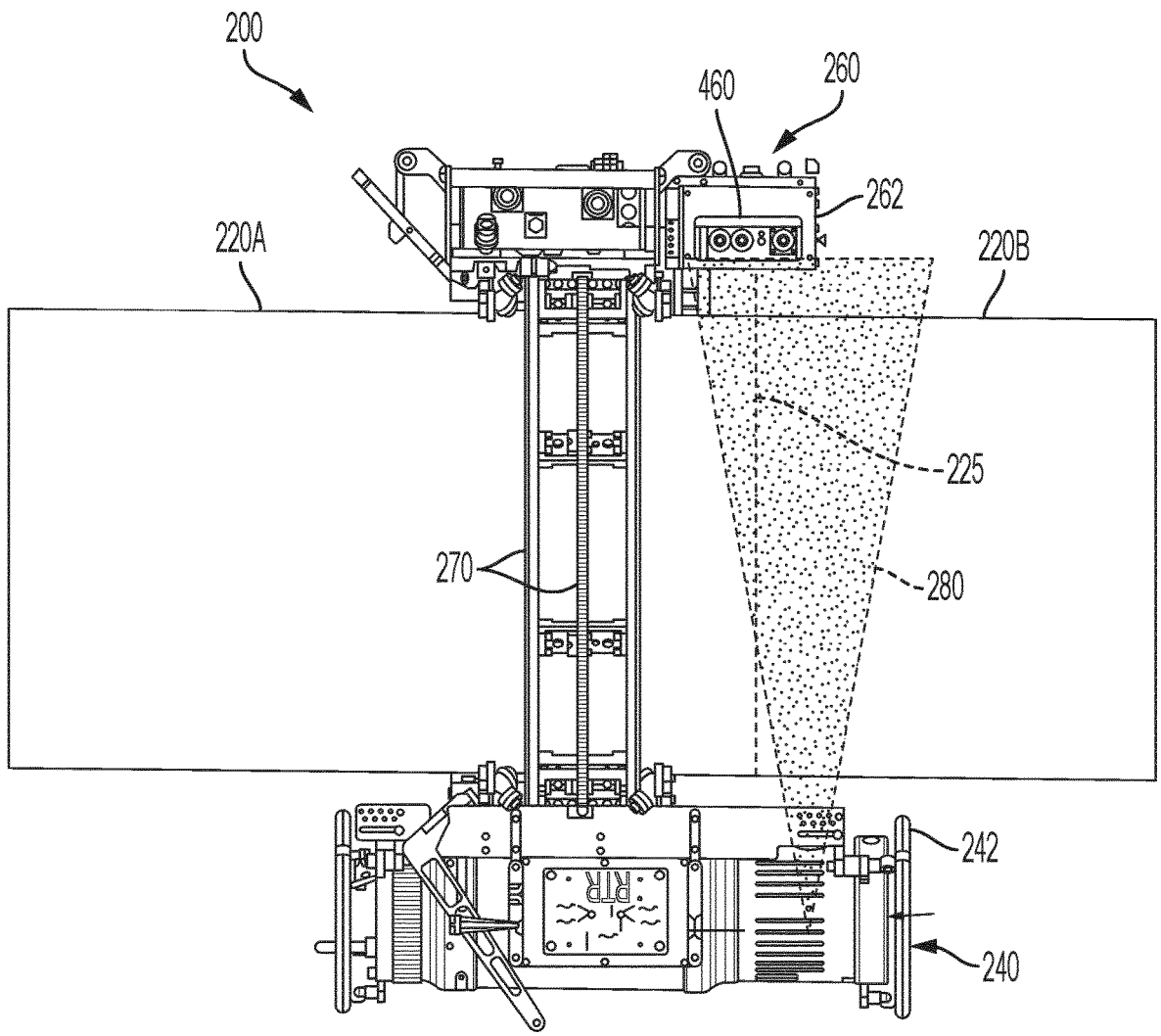
FIG. 3 shows a side view of the inspection system of FIG. 2.

FIG. 2 also shows that x-ray beam 280 projects in a generally cone-shaped manner outward from transmitter 240 toward receiver 260. As discussed above, beam 280 passes through pipe 220 twice, but of the two penetrations, the portion of the pipe nearest receiver 260 is the portion for which an inspection image is being prepared. FIG. 3 shows a side view of the inspection system of FIG. 2. A weld 225 to be inspected is disposed between pipe segment 220A and pipe segment 220B. Tack 270 is connected to pipe 220A on one side of weld 225. Transmitter 240 includes an emitter transmission portion 242. Emitter transmission portion 242 may extend or cantilever from pipe 220A over a portion of pipe 220B and including extension over weld 225. Similarly, cantilevered over weld 225 is receptor extension portion 262. Receptor extension portion 262 is an extension of receptor 260 and overlaps weld 225 longitudinally of pipe 220 so that as receptor 260 traverses pipe 220, receptor extension portion 262 remains just radially outward of the portion of the weld to be inspected. Specifically, as transmitter 240 transmits beam 280 toward and through the portion of pipe weld 225, receptor portion 260 is disposed just outside pipe 220B to receive the photons passing through that pipe weld portion. FIG. 3 also shows a dual detector module 460 of the present invention disposed in receptor extension portion 262. Operation of dual detector module 460 will be described in greater detail below.

Figure 4:
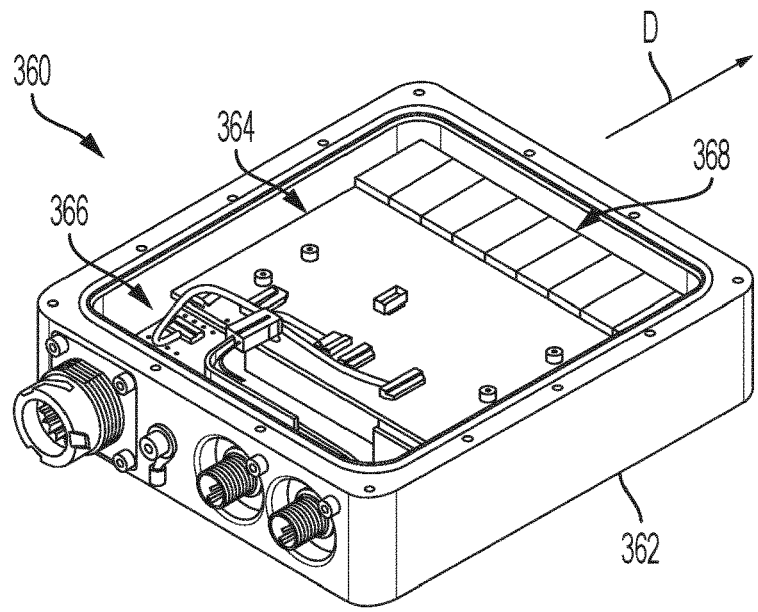
FIG. 4 shows a perspective view of a prior art detector portion of the inspection system of FIG. 1.

FIG. 4 shows a prior art detector module 360 in a face up configuration. Detector module 360 includes a housing 362 for housing various electromechanical parts. Detector module 360 also includes an electronic module 364. Electronic module 364 includes module circuit elements 366 and a plurality of sensors 368 (e.g., 8 sensors) that may be combined to form a sensor array. The array may be disposed along a distal edge of the module. When assembled, detector module 360 is connected to receptor extension portion 262 with a face thereof pointed toward or looking toward emitter transmission portion 242. Furthermore, when transmitter 240 and receiver 360 synchronously orbit pipe 220, detector module 360 travels in a direction D shown in FIG. 4.

Figure 5A:
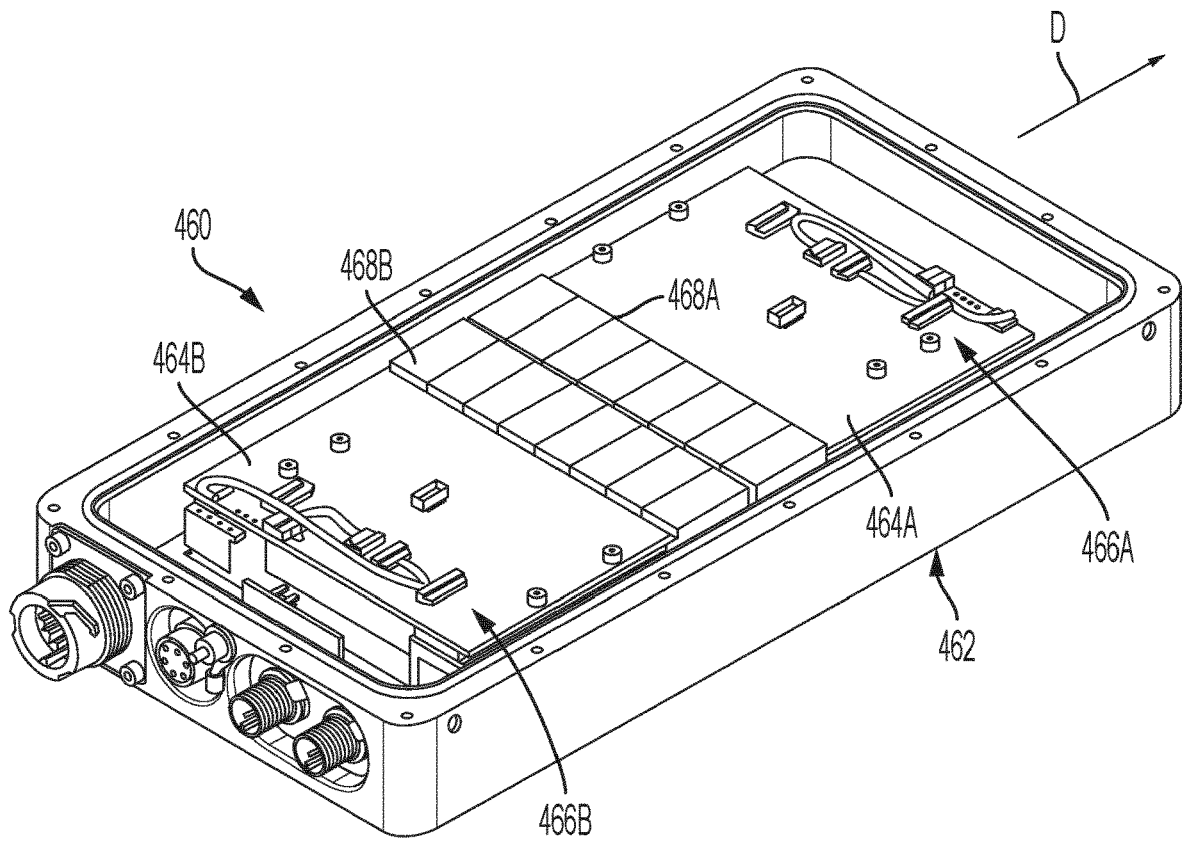
FIG. 5A shows a perspective view of a detector portion of the inspection system of FIG. 2.

For the reasons discussed in the background above, the array of detectors 368 are able to capture only a single series of photon patterns during a single continuous motion (e.g., constant speed) orbit of transmitter 140 and receiver 160. On the other hand, detector module 460 of the present invention shown in FIG. 3 and FIG. 5A is capable of generating data associated with multiple series of photon patterns. Detector module 460 includes a housing 462 for housing components of module 460. Dual detector module 460 also includes dual modules 464A and 464B. Modules 464A and 464B each respectively include module circuit elements 466A and 466B. Furthermore, Modules 464A and 464B each include a plurality of sensors 468A, 468B (e.g., 8 sensors each). Modules 464A and 464B may be arranged so that sensors 468A, 468B are adjacent, or back to back in housing 462. Specifically, the edge of modules 464A and 464B on which the respective plurality of sensors 468A, 468B are disposed may be positioned adjacent each other. When modules 464A and 464B are identical, such back to back positioning would represent a mirror image positioning of sensors 468A, 468B. Furthermore, a cost savings is achieved in an arrangement where only a single identical module may be utilized to achieve the claimed data doubling benefit.

Moreover, as housing 460 travels in direction D, sensors 468A are positioned to sense a photon pattern from a first weld segment (e.g., with a length in the D direction). Simultaneously, sensors 468B are positioned to sense a photon pattern from a second weld segment (e.g., also with a length in the D direction), immediately, adjacent to and lagging, the first weld segment. After some time advances, sensors 468B will advance in direction D to the same position of the pipe segment where sensors 468A just recorded a photon pattern. Each set of sensors 468A and 468B generates data that is processed and combined to build or generate a continuous photon pattern representing the 360° weld. However, one thing to consider is that the continuous photon pattern generated by sensors 468A will be slightly offset from the continuous photon pattern generated by sensors 468B by an amount related to the length (in the D direction) of sensors 468A which is at the particular weld portion first.

Figure 5B:
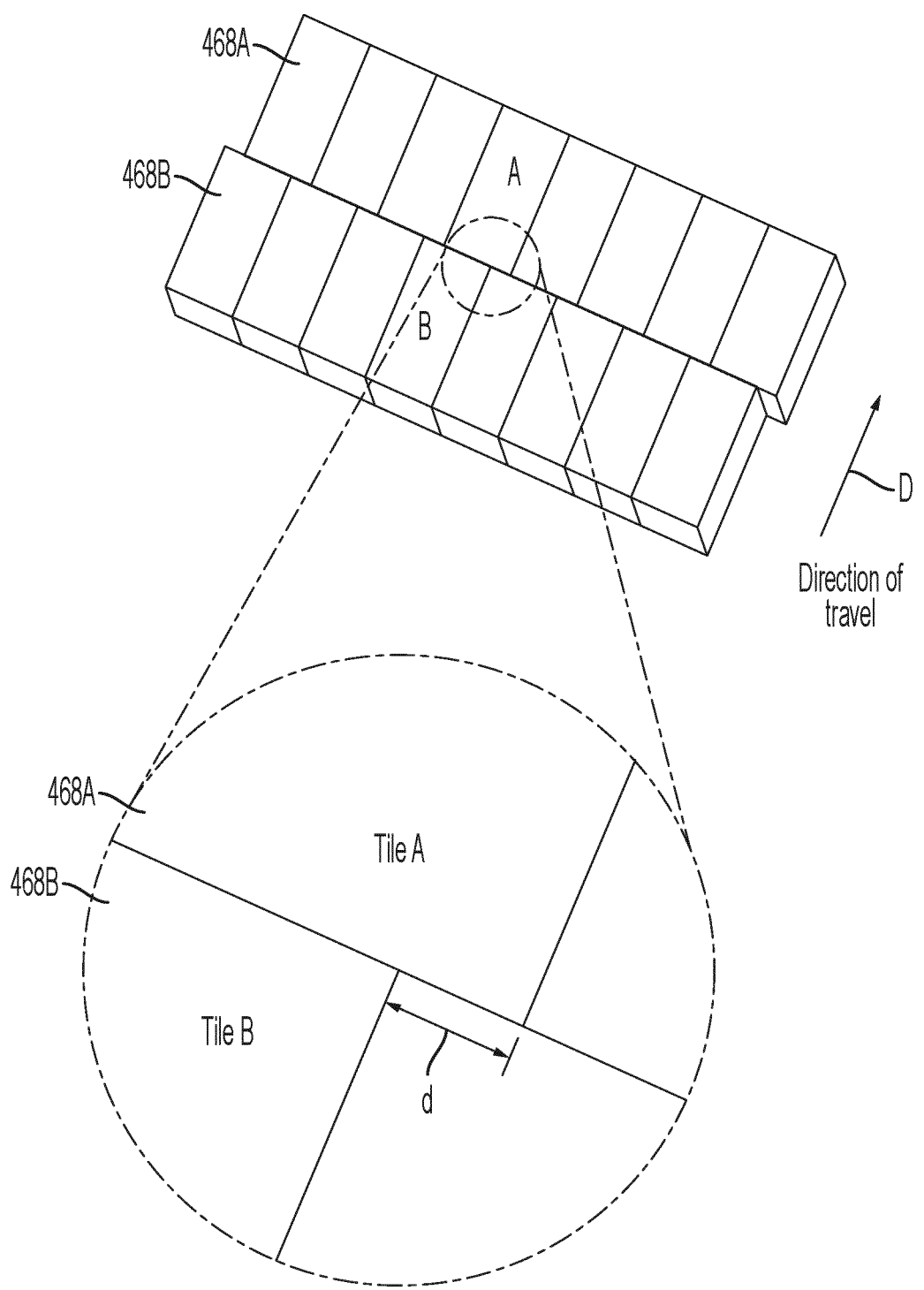
FIG. 5B shows two sensors of the inspection system of FIG. 2 offset in the direction perpendicular to the direction of movement.

FIG. 5B shows two adjacent sensor sets 468A and 458B offset in the direction transverse to the direction of motion of the housing 460. The tiles of the two sensors 468A, 468B may be bonded within a relative offset distance (d) between them. This distance (d) may be constant across devices within manufacturing tolerances.

When the two images from the two individual sensors 468A, 468B are superimposed, this distance is taken into account to best "align" the images. In other words, after image data from each sensor is store by a computer processor, the data may be manipulated to adjust for the offset. The adjustment may be a manual adjustment so that an inspector looking at the combined image may make small manual tweaks until the composite image looks best. During testing it was confirmed that the offset caused some blurring of image that was correctable with offset adjustments in the (d) direction. It could be said that the 2 sensors suffered a "parallax" error until correction the above descried offset techniques.

After numerous attempts over several days to capture focused images, a technique of imaging with individual sensors was developed. In that technique an inspector notes the individual images with the best resolution on the duplex IQI markers. The images may then be combined taking the d offset into consideration in the data calculations and in addition introduce a shift factor within a range (e.g., −4 μm to 4 μm) to achieve the maximum/best resolution. The introduction of the shift factor may be automatic by image processing techniques where the computer assesses the quality of the images (e.g., to optimize a shift factor). The best quality or best resolution combined image may also be achieved by manually adjusting the d offset (e.g., −4 μm to 4 μm) while observing the quality of the composite image on a display.

Figure 6:
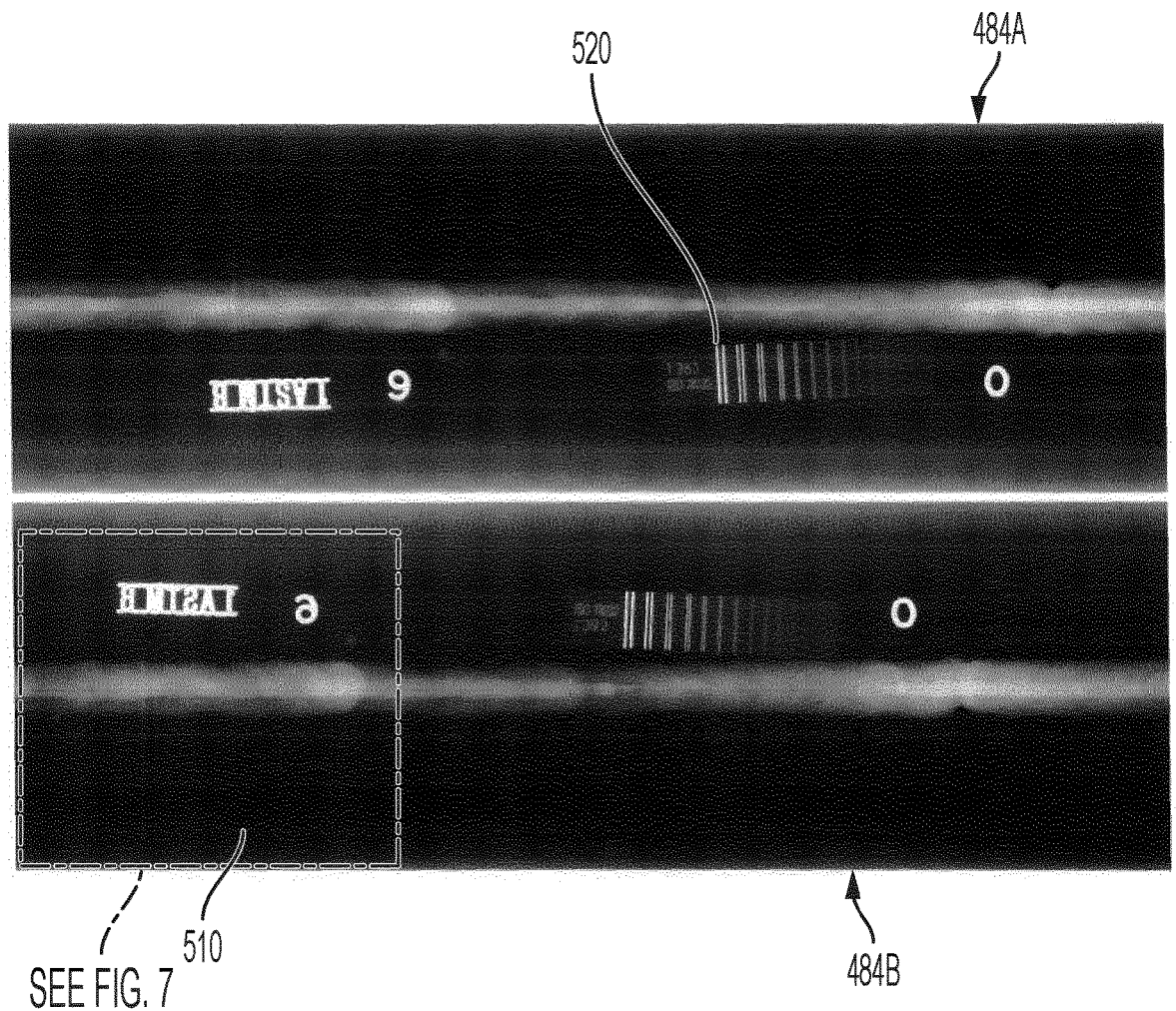
FIG. 6 shows two x-ray images of a portion of a weld taken by the inspection system of FIG. 2.

FIG. 6 shows an upper weld image 484A generated from dated derived from sensing a first series of photon patterns (i.e., using sensors 468A) and storing the data. FIG. 6 also shows a lower weld image 484B generated from data derived from sensing a second series of photon patterns (i.e., using sensors 468B) and storing the data. Stored data representing the first and second photon patterns series may be processed to generate further images. For example, in addition to using the data to generate individual images to observe their relative mirrored and offset relationship (as shown in FIG. 6), the stored data can be processed to generate one image superimposed over the other while correcting for mirroring and offset. It turns out that such a composite image provides significantly improved contrast and clarity over either of the images generated from a single photon pattern. The increased contrast of the improved image also enables a human or machine inspector to more easily and accurately identify potential anomalies and defects.

With respect to image processing, the present invention inspection system will now be described in more detail. A computer controller knows or calculates the speed of the transmitter 240 and receiver 260 and/or the circumferential distance travelled by the two around pipe 220. From this information, the controller periodically triggers sensors 468A, 468B to take a snapshot of the photon pattern of the photons passing through a portion of the weld at that instant. Each sensor (e.g., of the sixteen sensors on one module) includes an array of pixels with each pixel having dimensions (e.g., 0.1 mm2). Each pixel is capable of sensing or detecting a photon or density of photons. Therefore, at a front edge (based on the direction D) of sensors 468A is first row of pixels of 0.1 mm deep (in direction D) and multiple sensors wide (e.g., 8 sensors). On the same sensors and one row of pixels back is a second row of pixels of 0.1 mm depth. The time interval between a first snapshot and a next second snapshot may be the time period necessary for transmitter 240 and receiver 260 to move pixel row 2 up to where pixel row 1 was when snapshot 1 was taken. In other words, pixel row 1 sits behind a first weld portion and a snapshot of photon pattern data is taken. Then, the transmitter/receiver 240, 260 is rotated one pixel row to where the second pixel row is now behind that same weld portion and another snapshot is taken. A suitable transmitter/receiver 240, 260 speed is chosen and then snapshots are taken at time intervals necessary to allow advancement of a single pixel row distance until each pixel row on both sets of sensors 468A and 468B have generated photon pattern data for every weld portion of the weld. A single weld portion corresponding to a single pixel row.

Therefore, for each pixel, photon count or photon density information is paired with pixel location and stored. FIG. 6 shows a first weld image 484A generated from data sensed through sensors 468A and a second weld image 484B generated from data sensed through sensors 468B. However, a single image including all the photon pattern data could be generated. As discussed above, processing of the single combined weld image must include taking account for offset and mirrored relationship between modules 464A and 464B. By this method of utilizing two flipped modules 464A and 464B, the present invention is able to generate double the amount of data in the same amount of time (i.e., one rotation of the transmitter/receiver).

Figure 7:
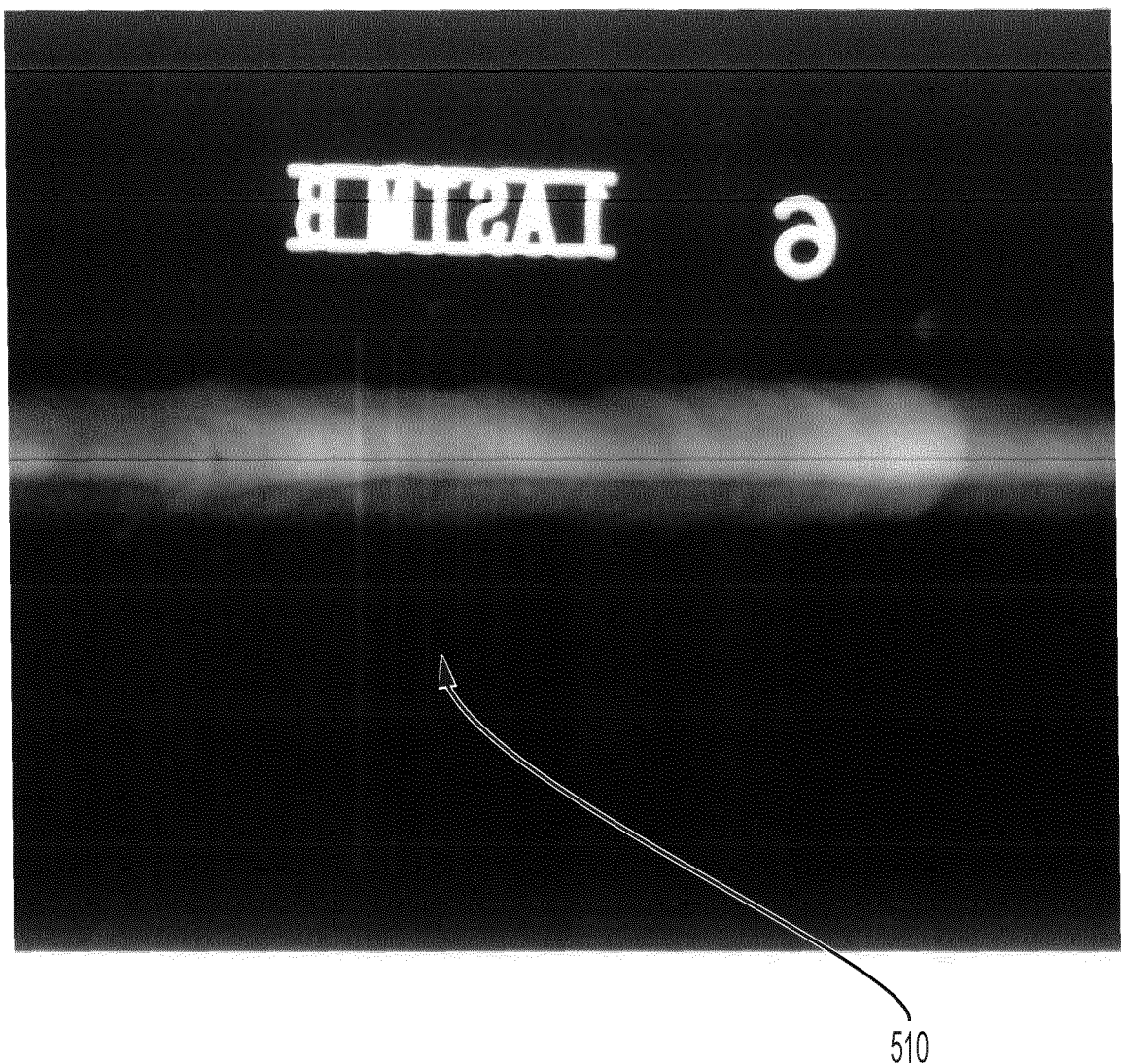
FIG. 7 illustrates an enlarged portion of the x-ray images of the lower left portion of FIG. 6 which better shows IQI lines.

Furthermore, the improved quality of a composite image generated using the techniques of the present invention are born out as standard IQI tests confirm improve improved image quality. IQI tests are well known and are performed in the x-ray weld inspection industry to provide a standard and/or baseline image for comparatively judging the quality of a weld image. Therefore, those processes will not be discussed in detail herein. An IQI object can be positioned near the weld (e.g., closest to the outer surface of a pipe to be imaged). An image of the IQI object is generated simultaneously and by the same means as the weld image. Each weld image may include the two above describe types of IQI indicators. For example, the IQI image may be a series of lines 510 (shown in FIG. 6) of progressively decreasing visibility. The first visible of the standard IQI lines indicates to an inspector the quality of the composite image (i.e., IQI image and weld image) and thus indicates the quality of the weld image. Similarly, IQI images may be derived from IQI objects that generate a series of double lines 520 (shown in FIG. 6) next to each other. Each double line is progressively less visibility. When the double lines become part of the composite image (i.e., the IQI image and the weld image) the first of the double lines that can be distinguished as two separate lines indicates the quality of the IQI and therefore also the weld images. FIG. 7 shows an enlarged image of a lower left corner of FIG. 6 which better shows IQI lines 510.

The above disclosure describes a process in which generally adjacent sensors (e.g., photosensors) separately detect images of a certain portion of a weld. Data representing each of the images is processed and the data is superimposed to generate a single image of better (e.g., sharper, better focused, more contrast, etc.) quality than either of the separate images individually. Because the image of a particular weld portion from the leading sensor is taken in time before the image of that same weld portion from the trailing sensor, the superimposition of the images will involve an offset shift of the images in the time direction to create a resultant focused image. However, offset shift in the time direction is not the only adjustment that can be made to improve the quality of the superimposed images derived from the image data of the separate sensors.

As the images are taken, the emitter and the two sensors may remain stationary relative to each other. However, because there is only one emitter and two sensors in two different locations, the perspective of the leading sensor as the emitter emits a single x-ray beam at both differently located sensors is different from the perspective of the second trailing sensor. The difference in perspective noticed by the two images results in two separate sensor image data sets that can be further corrected (e.g., before superposition) and superimposed. When a flashlight shines on two generally adjacent hands between the flashlight and a wall, the light from the flashlight casts two (not one) hand shaped images on the wall. This is because each hand has a different perspective relative to the flashlight. That different perspective is displayed on the wall as a hand shadow in two different places.

Because the emission of light travels in a straight line, we can use geometry (including the relative distances between the wall, the hand, and the flashlight) to predict/project alternate configurations (e.g., the size/shape of the images on the wall if the hand was closer to the wall). Images related to the data of each sensor can then be processed using such known geometric relationships so as to generate image data that compensates for the sensors having different perspectives relative to the emitter to produce image data as though both sensor perspectives were the same. After such compensating image(s) are generated, they may them be superimposed to produce a more accurate image than would be possible from a combination of the image data from separate perspectives.

Furthermore, as discussed above, a sensor is composed of a large array of pixels. Those pixels which are in different locations/regions on the sensor could be partitioned and treated as separate sensors. Therefore, the above-described processing that compensates for different location/perspectives can be applied to each specific partitioned array of pixels based on that array's specific location relative to the other partitioned pixels, the weld portion to be captured, and the position of the emitter.

In addition to the above-described image data processing that includes offsetting image data in the time direction and includes adjusting image data as though sensors in separate locations see the weld portion and emitter from the same perspective, image processing to identify the depth of a defect in the direction of the pipe thickness may be employed.

In general, when an x-ray image of a portion of a weld is generated as described above, the IQI marker is placed closest to an outer wall surface. An image is then taken of the weld portion and the IQI marker(s). However, if defects are visible on the two-dimensional image in the direction looking from the emitter to the sensor, the image does not indicate the depth of those defects in the direction of thickness of the pipe. In other words, the image does not include information that would teach an operator/inspector whether that defect is at or near the pipe outer wall, the pipe inner wall or somewhere in between. However, as mentioned above, with the emitter emitting x-rays in a straight line through the weld portion, the emitter essentially casts a shadow on the sensor which is detected and turned into image data. Because the geometry of the sensor location, the weld portion location, and the emitter location and direction is known, image data can be processed (e.g., extrapolated or interpolated) to generate secondary image data representing a projection of the original image data at various thickness levels of the pipe. For example, if the thickness of the pipe or pipe weld is (3) three centimeters, the geometry of the equipment (as mentioned above) could be used in calculations to process the originally sensed image data in order to calculate/predict secondary image(s) representing projections of the originally sensed image data at various wall thickness locations relative to the outer pipe wall where the IQI is located (e.g., 3 mm, 9 mm . . . 30 mm from the outer wall). Upon inspection of the 10 generated projected secondary images for defects or anomalies (e.g., by an inspector or by a computer), the depth associated the image in which the defect is best focussed will better/best define the depth of the defect in the direction of pipe thickness.

Furthermore, image processing computers can utilize techniques such as tomosynthesis, laminography, and focus tracking to manipulate data in order to compensate for the shortcomings of the equipment or equipment arrangement from which the original data is derived.

The embodiments of the present invention described above are intended to be examples only. The present invention may be embodied in other specific forms. Alterations, modifications and variations to the embodiments may be made without departing from the intended scope of the present invention. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology.

The invention claimed is:

1. An x-ray imaging system for generating images of a pipe weld from which weld quality defects may be detected, the system comprising:
   an x-ray emitter for emitting a beam of x-ray photons in a projection pattern;
   a first photon detector for sensing a first detection pattern of photons emitted from the x-ray emitter and passing through a portion of the weld;
   a second photon detector for sensing a second detection pattern of photons emitted from the x-ray emitter and passing through the portion of the weld;
   an orbital travel assembly for supporting the x-ray emitter and the first and second photon detectors as they travel along an orbital weld path of the weld at least partly around the pipe in a direction of travel;
   wherein the second photon detector is positioned behind the first photon detector in the direction of travel along the orbital weld path, such that the second photon detector is configured to sense the second detection pattern after the first photon sensor detects the first detection pattern,
   wherein the x-ray imaging system further comprises a detector module,
   wherein the detector module comprises a module housing containing the first and second photon detectors, and
   wherein the first photon detector comprises a first electronic module including an array of a plurality of photon sensors for sensing the first detection pattern of photons,
   wherein the second photon detector comprises a second electronic module including an array of a plurality of photon sensors for sensing the second detection pattern of photons, and
   wherein the first electronic module is positioned in an opposing orientation relative to the second electronic module such that the sensed first and second detection patterns of photons are substantially mirror images of each other.

2. An x-ray imaging system for generating images of a pipe weld from which weld quality defects may be detected, the system comprising:
   an x-ray emitter for emitting a beam of x-ray photons in a projection pattern;
   a first photon detector for sensing a first detection pattern of photons emitted from the x-ray emitter and passing through a portion of the weld;
   a second photon detector for sensing a second detection pattern of photons emitted from the x-ray emitter and passing through the portion of the weld;
   an orbital travel assembly for supporting the x-ray emitter and the first and second photon detectors as they travel along an orbital weld path of the weld at least partly around the pipe in a direction of travel;

wherein the second photon detector is positioned behind the first photon detector in the direction of travel along the orbital weld path, such that the second photon detector is configured to sense the second detection pattern after the first photon sensor detects the first detection pattern, wherein the x-ray imaging system further comprise a memory device configured to receive and record data representing the first detection pattern of photons and data representing the second detection pattern of photons, and wherein the x-ray imaging system is configured such that the data representing the first detection pattern of photons is projected onto a visual display and the data representing the second detection pattern of photons is simultaneously also projected onto the visual display to superimpose the first and second detection patterns.

3. An x-ray imaging system according to claim 2, wherein the x-ray imaging system is configured such that the position of the first detection pattern of photons is adjusted with respect to the position of the second detection pattern of photons in order to match the images and correct for an offset caused by the second detection pattern being generated after the first detection pattern.

4. A method of generating an x-ray image of a pipe weld for detecting a defect in the weld by inspection of the x-ray image, including the steps of:
providing an x-ray photon emitter;
providing a first photon detector for sensing a first detection pattern of photons projected from the x-ray photon emitter;
providing a second photon detector for sensing a second detection pattern of photons projected from the x-ray photon emitter;
causing the first and second photon detectors to travel along an orbital weld path of the weld at least partly around the pipe in a direction of travel;
projecting photons from the x-ray photon emitter through a portion of the weld and onto the first photon detector to sense the first detection pattern and to generate data representing the first detection pattern;
after detecting the first detection pattern, projecting photons from the x-ray photon emitter through the portion of the weld and onto the second photon detector to sense the second detection pattern and to generate data representing the second detection pattern; and
superimposing the first and second detection patterns onto each other and adjusting the two patterns for offset so that the first detection pattern is synced with the second detection pattern.

5. A method according to claim 4, wherein the step of superimposing the first and second detection patterns and adjusting the two patterns for offset so that the first detection pattern is synced with the second detection pattern, comprises adjusting the offset position of the two patterns in the direction of travel so that the first detection pattern is synced in the direction of travel with the second detection pattern.

6. A method according to claim 4, wherein the step of superimposing the first and second detection patterns and adjusting the two patterns for offset so that the first detection pattern is synced with the second detection pattern, comprises adjusting the offset position of the two patterns in a direction which is transverse to the direction of travel so that the first detection pattern is synced in the transverse direction with the second detection pattern.

7. An x-ray imaging system for generating images of a pipe weld from which weld quality defects may be detected, the system comprising:
an x-ray emitter for emitting a beam of x-ray photons in a projection pattern;
a photon detector for sensing a first detection pattern of photons emitted from the x-ray emitter and passing through a portion the weld;
an orbital travel assembly for supporting the x-ray emitter and the photon detector as they travel along an orbital weld path of the weld at least partly around the pipe in a direction of travel;
an image processing computer;
wherein the photon detector is configured to sense the first detection pattern of photons passing through the portion of the weld and the image processing computer is configured to store data associated with the first detection pattern;
wherein the image processing computer is configured to process data from the first detection pattern and a geometry of the relative positions of the portion of the weld and the photon detector to generate a second detection pattern; and
wherein the second detection pattern is associated with a location of a portion of the weld in a direction of thickness of the pipe that is a distance from an outer surface of the pipe.

8. An x-ray imaging system according to claim 7, wherein the image processing computer is also configured to process data from a position of the x-ray emitter relative to the portion of the weld and/or relative to the photon detector to generate the second detector pattern.

9. An x-ray imaging system according to claim 7, wherein the image processing computer is configured to process data from the first detection pattern and a geometry of the relative positions of the portion of the weld and the photon detector to generate a plurality of second detection patterns, each of the second detection patterns associated with the location of the portion of the weld in the direction of thickness of the pipe.

10. An x-ray imaging system according to claim 9, wherein the image processing computer is configured to process data from the first detection pattern and/or the plurality of detection patterns to determine the location of one or more defects or anomalies.

11. An x-ray imaging system according to claim 9, wherein the x-ray imaging system is configured to identify one or more defects if present, and
wherein the image processing computer is configured to determine in which of the plurality of detection patterns the, or each, defect is best focused.

12. An x-ray imaging system according to claim 11, wherein the x-ray imaging system is configured such that an image of the portion of the weld is displayed and
wherein the location of the defect in the direction of thickness is identified.

* * * * *